United States Patent [19]

Schumacher

[11] Patent Number: 4,993,951
[45] Date of Patent: Feb. 19, 1991

[54] CERAMIC BODY FOR A PRE-DRILLED TOOTH CAVITY

[76] Inventor: Dieter Schumacher, Bessler Strasse 5, 2370 Rendsburg, Fed. Rep. of Germany

[21] Appl. No.: 288,092

[22] Filed: Dec. 21, 1988

[30] Foreign Application Priority Data

Dec. 21, 1988 [DE] Fed. Rep. of Germany ....... 3743433

[51] Int. Cl.$^5$ .................................................. A61C 5/04
[52] U.S. Cl. .................................. 433/226; 433/228.1
[58] Field of Search ...................... 433/215, 226, 228.1, 433/197

[56] References Cited

U.S. PATENT DOCUMENTS

| | | | |
|---|---|---|---|
| 866,305 | 9/1907 | Roach | 433/226 |
| 1,063,376 | 6/1913 | Nies | 433/226 |
| 1,118,301 | 11/1914 | Magill | 433/226 |
| 1,211,244 | 1/1917 | Schroeder et al. | 433/226 |
| 4,017,454 | 4/1977 | Müller | 433/228.1 |
| 4,234,310 | 11/1980 | Leuthard | 433/228.1 |
| 4,355,980 | 10/1982 | Dwight | 433/226 |

FOREIGN PATENT DOCUMENTS

| | | | |
|---|---|---|---|
| 3720308 | 12/1988 | Fed. Rep. of Germany | 433/226 |
| 16126 | of 1903 | United Kingdom | 433/226 |

*Primary Examiner*—John J. Wilson
*Assistant Examiner*—Michael Lynch
*Attorney, Agent, or Firm*—Herbert W. Larson

[57] ABSTRACT

Purposely made ceramic body for filling a pre-drilled cavity in a decayed, especially caries-ridden, tooth. The ceramic body has a roughly beam-shaped, tapered, blunt wedge-shaped, downward-pointing segment and an upward-pointing dove-tailed extension segment with an obtuse-angled notch forming a fissure in the upper surface of the body.

7 Claims, 2 Drawing Sheets

CERAMIC BODY FOR A PRE-DRILLED TOOTH CAVITY

BACKGROUND OF THE INVENTION

The invention relates to a ceramic body purposely made to fill a pre-drilled cavity in a decayed, especially caries-ridden, tooth.

Ceramic bodies purposely made for filling cavities are already familiar from German Patent No. 146,660. However these have failed to gain acceptance in practice.

SUMMARY OF THE INVENTION

The aim of the invention is the creation of a purposely made ceramic body, which meets practical requirements.

According to the invention this aim is achieved by a roughly beam-shaped segment with a downward-pointing, tapered, blunt wedge-shaped cross-section extending into an upward-pointing dovetailed segment with a fissure-forming, obtuse-angled notch in the upper surface of the body.

One of the remarkable features of a preferred embodiment is the fact that the blunt edge-shaped segment and/or the dovetail-shaped segment in the region of at least one of the two end walls of the body is formed so as to be lengthened in a downward or an outward direction respectively. Alternatively, however, a disc matched to the end wall of the body could be provided, equipped with a gap corresponding to the cross-section of the body.

Further, it is suggested that the body be made of a translucent material.

DETAILED DESCRIPTION OF THE DRAWINGS

Figure 2:
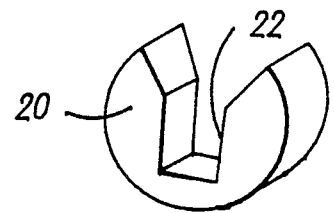
Figure 1:
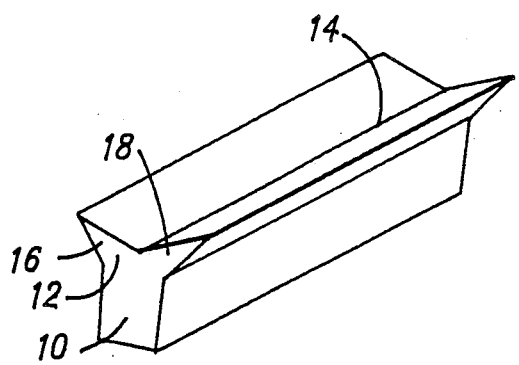
Figure 5:
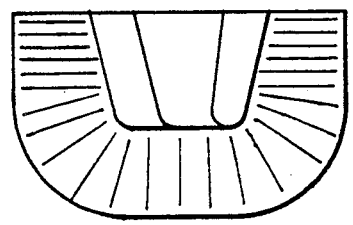
Figure 4:
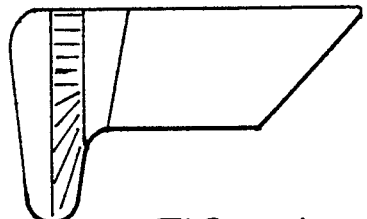
Figure 3:
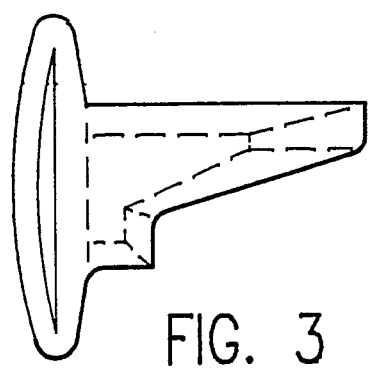
Figure 6:
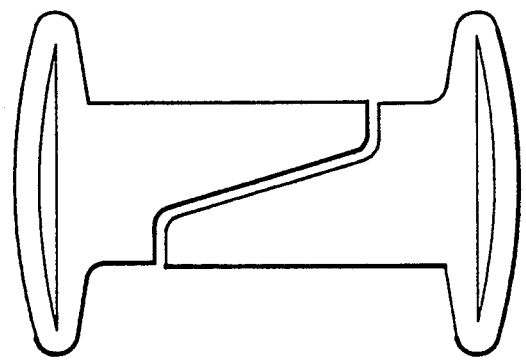

In the following the invention is explained with reference to a drawing representing two embodiments. This shows:

FIG. 1 is a first embodiment of the invention shown in perspective,

FIG. 2 an illustration of the disc matching the end wall of the body,

FIG. 3 a top view of an alternative design of the purposely made body,

FIG. 4 a side view of the purposely made body shown in FIG. 3,

FIG. 5 an illustration of the purposely made body shown i FIGS. 3 and 4 seen in the direction of the arrow V, and FIG. 6 an illustration of the combination of two such purposely made bodies arranged symmetrically to each other.

FIGS. 7 to 10 illustrate of different types of purposely made bodies.

DETAILED DESCRIPTION OF THE INVENTION

The proposed purposely made ceramic body comprises a blunt wedge-shaped segment 10, whose form is tapered downwards. The blunt wedge-shaped segment 10 supports a dovetailed segment 12, which is shaped into two outward-pointing projections 16 and 18. The area between the tips of the projections 16 and 18 is shaped like an obtuse-angled notch, such that a fissure 14 is formed.

FIG. 2 shows a disc 20, which is provided with a gap whose cross-section corresponds to that o[the body. Such discs are inserted prior to the fitting of the beam into the region of the sides of the cavity; thereupon the purposely made body is inserted from above into the gap 22 of the disc 20 and connected with the latter via the application of a composite or cement.

FIGS. 3, 4 and 5 show views of an alternative embodiment. In this embodiment the body has already been provided with the upward and outward stretching extensions in its frontal region.

FIG. 6 clarifies how two such purposely made bodies are put together to fill out the entire cavity.

The proposed shape of the purposely made body with a conically tapering section 10 enables a reliable fitting of the purposely made body in the cavity. Reliable adhesion is assured by a sufficient roughness of the lateral surfaces, which can be achieved by cauterization or the like. The provision of a dovetail-shaped segment 12 formed into points 16 and 18 above the blunt wedge-shaped segment 10 makes it possible for the prefabricated body to form the chewing surface, whereby the force exerted on segments 16 and 18 is conducted inwards.

Figure 7:
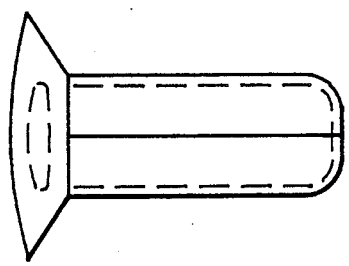
Figure 8:
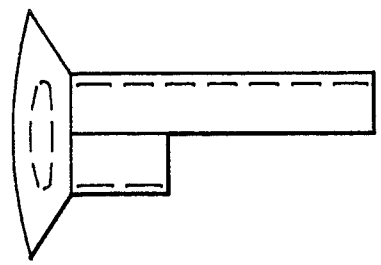
Figure 9:
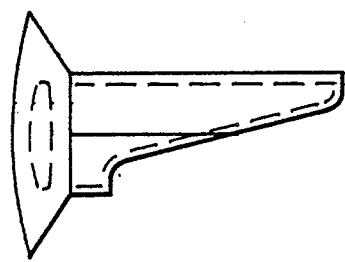
Figure 10:
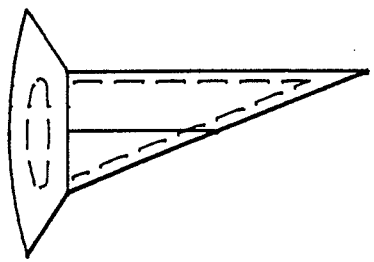

It goes without saying that the extension only needs to be arranged on one of the two frontal sides of the body (FIG. 7). In such a configuration a shorter ceramic body can also be inserted from both sides The other ends of the beam-shaped segment thereby comprise a stepped or slanting form, such that they can be arranged to partly overlap. Different purposely made bodies with stepped or slanting legs are shown in FIGS. 8 to 10.

The proposed prefabricated, purposely made body is equivalent in its form to a cavity formed in accordance with the currently valid rules for drilling. After insertion it fills up the greater part of the cavity and is connected to the stump of the tooth via a composite.

The advantage in using such a purposely made body is that the space, which is to be filled with a malleable filling material such as amalgam, cement or composite, is clearly reduced. The resistance to corrosion on the occlusion area is clearly increased. By virtue of the fact that only a little composite material is used the contraction of the filling material is considerably reduced. A fracture of the filling is practically impossible.

The purposely made ceramic body, inserted in the cavity in the familiar manner, preferably with the use of a composite or cement thus enables the usage of far less filling material. The effects of contraction are thereby largely avoided, whilst the firmness of the filling is considerably increased.

By using a light-conducting oxide ceramic the use of a composite hardened by light is enabled.

As the material for the purposely made body an oxide ceramic is most useful. This will preferably be coated with a dental ceramic.

The purposely made body comprising the invention can be inserted directly into the cavity by the dentist and stuck onto the tooth by using a composite. Alternatively, however, the dentist can produce a duplicate of the tooth, the dental technician manufacturing a mold out of dental ceramic, in which the purposely made body of the invention comprises the core. After cauterization of the cast thus formed the dentist inserts it into the tooth by using a composite or cement.

I claim:

1. A ceramic body having two end walls made for filling a predrilled cavity in a decayed especially caries-ridden, tooth, comprising a roughly beam-shaped, tapered, blunt wedge-shaped, downward-pointing segment and an upward-pointing dove-tailed extension segment with an obtuse-angled notch forming a fissure in the upper surface of the body.

2. A ceramic body according to claim 1, characterized in that the blunt wedge-shaped segment is lengthened in a downward direction in the region of at least one of the end walls of the body.

3. A ceramic body according to claim 1, characterized in that the dove-tailed segment widens outwards in the region of at least one of the end walls of the body.

4. A ceramic body according to claim 1, characterized by adding as a base in the cavity a disc matching in complimentary shape to the pair of walls of the body, the disc provided with a gap corresponding to a cross-section of the body for receiving the wedge-shaped segment.

5. A ceramic body according to claim 4, characterized in that the disc is convex shapes on at least one side.

6. A ceramic body according to claim 1, characterized in that the body is made of a translucent material 7. A ceramic body according to claim 1, characterized in that one end of the beam-shaped segment is in a stepped or slanting form.

* * * * *